US012383640B2

(12) United States Patent
Brockschmidt, Jr. et al.

(10) Patent No.: US 12,383,640 B2
(45) Date of Patent: Aug. 12, 2025

(54) ULTRAVIOLET LIGHT-EMITTING ASSEMBLY

(71) Applicant: The Boeing Company, Chicago, IL (US)

(72) Inventors: Arthur E. Brockschmidt, Jr., Renton, WA (US); Jamie J. Childress, Mercer Island, WA (US)

(73) Assignee: The Boeing Company, Arlington, VA (US)

( * ) Notice: Subject to any disclaimer, the term of this patent is extended or adjusted under 35 U.S.C. 154(b) by 926 days.

(21) Appl. No.: 17/452,564

(22) Filed: Oct. 27, 2021

(65) Prior Publication Data

US 2022/0184251 A1 Jun. 16, 2022

Related U.S. Application Data

(60) Provisional application No. 63/154,239, filed on Feb. 26, 2021, provisional application No. 63/124,341, filed on Dec. 11, 2020.

(51) Int. Cl.
| | |
|---|---|
| *A61L 2/10* | (2006.01) |
| *A61L 2/26* | (2006.01) |
| *F21V 21/14* | (2006.01) |
| *F21V 23/00* | (2015.01) |
| *F21V 29/74* | (2015.01) |

(52) U.S. Cl.
CPC ............... *A61L 2/10* (2013.01); *A61L 2/26* (2013.01); *F21V 21/14* (2013.01); *F21V 23/003* (2013.01); *F21V 29/74* (2015.01); *A61L 2202/11* (2013.01)

(58) Field of Classification Search
None
See application file for complete search history.

(56) References Cited

U.S. PATENT DOCUMENTS

| | | |
|---|---|---|
| 5,498,394 A | 3/1996 | Matschke |
| 5,594,304 A | 1/1997 | Graber |
| 5,660,719 A | 8/1997 | Kurtz et al. |
| 6,144,175 A | 11/2000 | Parra |

(Continued)

FOREIGN PATENT DOCUMENTS

| | | |
|---|---|---|
| CA | 2967190 A1 | 5/2016 |
| CA | 3123597 A1 | 6/2020 |

(Continued)

OTHER PUBLICATIONS

Souza et al., Study of the Influence of Variation in Distances Between Electrodes in Spectral DBD Plasma Excitation, Materials Research. 2016; 19(1): 202-206 (Year: 2016).*

(Continued)

*Primary Examiner* — Holly Kipouros
(74) *Attorney, Agent, or Firm* — Alleman Hall & Tuttle LLP

(57) ABSTRACT

Assemblies and methods for disinfecting surfaces using ultraviolet (UV) light are disclosed. In one aspect, a UV light-emitting assembly comprises a plurality of UV light emitters, and first and second UV light emitter supports seating the UV light emitters. A first heat sink is affixed to the first UV light emitter support and a second heat sink is affixed to the second UV light emitter support. A thermally conductive and electrically insulating plate contacts the first heat sink and the second heat sink.

22 Claims, 11 Drawing Sheets

(56) References Cited

U.S. PATENT DOCUMENTS

| | | | |
|---|---|---|---|
| 6,656,424 | B1 | 12/2003 | Deal |
| 7,595,723 | B2 | 9/2009 | Heitzmann et al. |
| 8,581,522 | B2 | 11/2013 | Inskeep |
| 8,791,441 | B1 | 7/2014 | Lichtblau |
| 8,834,805 | B2 | 9/2014 | Owen et al. |
| 9,623,133 | B2 | 4/2017 | Childress et al. |
| 11,382,993 | B2 | 7/2022 | Childress |
| 2004/0249369 | A1 | 12/2004 | Muzzi et al. |
| 2005/0152146 | A1* | 7/2005 | Owen ............... F21V 29/57 362/294 |
| 2005/0158206 | A1* | 7/2005 | Moisan ............... A61L 2/14 422/186.21 |
| 2008/0152548 | A1 | 6/2008 | Clark et al. |
| 2008/0260601 | A1 | 10/2008 | Lyon |
| 2008/0289800 | A1 | 11/2008 | Simadiris et al. |
| 2009/0045750 | A1 | 2/2009 | Brggs et al. |
| 2011/0243789 | A1 | 10/2011 | Roberts |
| 2012/0051030 | A1 | 3/2012 | Johnson |
| 2012/0076702 | A1 | 3/2012 | Dunkley et al. |
| 2012/0168641 | A1 | 7/2012 | Lizotte |
| 2012/0240968 | A1 | 9/2012 | Schumacher |
| 2012/0305787 | A1 | 12/2012 | Henson |
| 2013/0330235 | A1 | 12/2013 | Stibich et al. |
| 2014/0044590 | A1 | 2/2014 | Trapani |
| 2014/0175280 | A1 | 6/2014 | Tantillo |
| 2014/0320009 | A1 | 10/2014 | Goscha et al. |
| 2015/0064065 | A1 | 3/2015 | Kreitenberg |
| 2015/0165079 | A1 | 6/2015 | Shur et al. |
| 2015/0182647 | A1 | 7/2015 | Ranta et al. |
| 2015/0235727 | A1 | 8/2015 | Lott et al. |
| 2016/0271288 | A1 | 9/2016 | Davis |
| 2016/0324996 | A1 | 11/2016 | Bilenko et al. |
| 2017/0198896 | A1 | 7/2017 | May |
| 2018/0064833 | A1 | 3/2018 | Childress et al. |
| 2018/0133351 | A1 | 5/2018 | Smetona et al. |
| 2018/0243582 | A1 | 8/2018 | Kaneda et al. |
| 2018/0339075 | A1 | 11/2018 | Kennedy et al. |
| 2019/0142981 | A1 | 5/2019 | Kim et al. |
| 2019/0300174 | A1 | 10/2019 | Young et al. |
| 2020/0061223 | A1 | 2/2020 | Hallack |
| 2020/0234941 | A1 | 6/2020 | Yagyu et al. |
| 2020/0289698 | A1 | 9/2020 | Polidoro |
| 2021/0213147 | A1 | 7/2021 | Donhowe et al. |
| 2021/0338860 | A1 | 11/2021 | Grenon et al. |
| 2021/0346540 | A1 | 11/2021 | Childress et al. |
| 2021/0346541 | A1 | 11/2021 | Callahan et al. |
| 2021/0346561 | A1 | 11/2021 | Callahan et al. |
| 2021/0361794 | A1 | 11/2021 | Yencho |
| 2021/0386882 | A1 | 12/2021 | Brockschmidt, Jr. et al. |
| 2021/0386883 | A1 | 12/2021 | Childress |
| 2021/0386884 | A1 | 12/2021 | Brockschmidt, Jr. et al. |
| 2021/0396918 | A1 | 12/2021 | Gross et al. |
| 2022/0023458 | A1 | 1/2022 | Brockschmidt, Jr. et al. |
| 2022/0023459 | A1 | 1/2022 | Colletti et al. |
| 2022/0023478 | A1 | 1/2022 | Childress |
| 2022/0068627 | A1 | 3/2022 | Yagyu et al. |
| 2022/0111086 | A1 | 4/2022 | Childress |
| 2022/0111087 | A1 | 4/2022 | Childress et al. |
| 2022/0111096 | A1 | 4/2022 | Childress |
| 2022/0113006 | A1 | 4/2022 | Childress et al. |
| 2022/0133925 | A1 | 5/2022 | Gray et al. |
| 2022/0184252 | A1 | 6/2022 | Childress et al. |
| 2023/0258315 | A1* | 8/2023 | Shinoda ............... H01J 61/30 252/588 |

FOREIGN PATENT DOCUMENTS

| | | |
|---|---|---|
| CN | 202342524 U | 7/2012 |
| CN | 106049005 A | 10/2016 |
| CN | 211204004 U | 8/2020 |
| CN | 111744026 A | 10/2020 |
| DE | 3910653 A1 | 10/1990 |
| JP | H09201401 A | 8/1997 |
| JP | 2000283840 A | 10/2000 |
| JP | 2002100323 A | 4/2002 |
| JP | 2018055965 A | 4/2018 |
| JP | 2018092755 A | 6/2018 |
| JP | 2018167166 A | 11/2018 |
| KR | 1020120083541 A | 7/2012 |
| KR | 20150045628 A | 4/2015 |
| WO | 2012142427 A1 | 10/2012 |
| WO | 2015028334 A1 | 3/2015 |
| WO | 2016210399 A2 | 12/2016 |
| WO | 2020052506 A1 | 3/2020 |

OTHER PUBLICATIONS

United States Patent and Trademark Office, Office Action Issued in U.S. Appl. No. 17/452,559, filed Feb. 1, 2024, 39 pages.
European Patent Office, Office Action Issued in Application No. 21210726.2, Sep. 14, 2023, Germany, 9 pages.
European Patent Office, Office Action Issued in Application No. 21210723.9, Sep. 19, 2023, Germany, 5 pages.
European Patent Office, Office Action Issued in Application No. 21210728.8, Sep. 20, 2023, Germany, 5 pages.
Plass, C. et al., "Ultraviolet Wand," U.S. Appl. No. 29/735,235, filed May 19, 2020, 15 pages.
Barrett, L. et al., "Sterilization of sea lice eggs with ultraviolet C light: towards a new preventative technique for aquaculture," Post Management Science, vol. 76, No. 3, Mar. 2020, 7 pages.
European Patent Office, Extended European Search Report issued in application No. 21202296.6, May 24, 2022, Germany, 11 pages.
European Patent Office, Extended European Search Report issued in application No. 21207466.0, May 2, 2022, Germany, 8 pages.
European Patent Office, Extended European Search Report issued in application No. 21210410.03, Apr. 25, 2022, Germany, 10 pages.
Honeywell UV Treatment System, Available online at https://aerospace.honeywell.com/en/learn/products/cabin/uv-cabin-system, Available as early as Jun. 21, 2021, 4 pages.
Huang, B. et al., "Research on UV radiation measurements and correction methods," Proceedings of the International Symposium on Photoelectronic Detection and Imaging, May 24, 2011, Beijing, China, 10 pages.
ISA United States Patent Office, Written Opinion issued in application No. PCT/US2016/039506, May 31, 2017, WIPO, 8 pages.
European Patent Office, partial European Search Report issued in application No. 21202296.6, Mar. 4, 2022, Germany, 11 pages.
"UVC Sensors to Monitor Ultraviolet Germicidal Irradiation {UVGI}," Available online at https://www.pro-lite.co.uk/File/Solar%20Light%20UVGI%20Radiometer%20Brochure.pdf, Jan. 2019, 2 pages.
European Patent Office, Partial European Search Report Issued in Application No. 21210723.9, May 12, 2022, Germany, 16 pages.
United States Patent and Trademark Office, Office Action Issued in U.S. Appl. No. 17/452,561, filed Jan. 3, 2024, 60 pages.
European Patent Office, Extended European Search Report Issued in Application No. 21210725.4, Sep. 6, 2022, Germany, 79 pages.
European Patent Office, Extended Search Report Issued in Application No. 21210726.2, Sep. 8, 2022, Germany, 52 pages.
European Patent Office, Extended Search Report Issued in Application No. 21210727.0, Sep. 9, 2022, Germany, 16 pages.
European Patent Office, Extended Search Report Issued in Application No. 21210723.9, Sep. 23, 2022, Germany, 21 pages.
European Patent Office, Extended European Search Report Issued in Application No. 21210728.8, Sep. 28, 2022, Germany, 13 pages.
Welch, D. et al., "Far-UVC light: A new tool to control the spread of airborne-mediated microbial diseases," Scientific Reports, vol. 8, No. 1, Feb. 9, 2018, 7 pages.
"Ushio Care222, Far UV-C Disinfection Technology," Ushio, Oct. 3, 2020, 5 pages.
European Patent Office, Partial European Search Report Issued in Application No. 21210725.4, Apr. 26, 2022, Germany, 16 pages.
European Patent Office, Partial European Search Report Issued in Application No. 21210726.2, May 3, 2022, Germany, 17 pages.
European Patent Office, Partial European Search Report Issued in Application No. 21210727.0, May 4, 2022, Germany, 16 pages.

(56) References Cited

OTHER PUBLICATIONS

Buonanno, M. et al., "Far-UVC light (222nm) efficiently and safely inactivates airborne human coronaviruses," Scientific Reports, vol. 10, Jun. 24, 2020, 8 pages.
European Patent Office, Partial European Search Report Issued in Application No. 21210728.8, Jun. 9, 2022, Germany, 14 pages.
United States Patent and Trademark Office, Notice of Allowance Issued in U.S. Appl. No. 17/452,560, filed Mar. 1, 2024, 41 pages.
United States Patent and Trademark Office, Notice of Allowance Issued in U.S. Appl. No. 17/452,561, filed Apr. 2, 2024, 19 pages.
United States Patent and Trademark Office, Office Action Issued in U.S. Appl. No. 17/452,555, filed Nov. 22, 2024, 53 pages.
United States Patent and Trademark Office, Office Action Issued in U.S. Appl. No. 17/464,792, filed Jan. 16, 2025, 46 pages.

\* cited by examiner

ULTRAVIOLET LIGHT-EMITTING ASSEMBLY

CROSS REFERENCE TO RELATED APPLICATIONS

This application claims priority to U.S. Provisional Patent Application Ser. No. 63/154,239, filed Feb. 26, 2021, and to U.S. Provisional Patent Application Ser. No. 63/124,341, filed Dec. 11, 2020, the entirety of which are hereby incorporated herein by reference for all purposes.

FIELD

This disclosure generally relates to disinfecting surfaces, and more particularly to assemblies and methods for disinfecting surfaces using ultraviolet (UV) light.

BACKGROUND

Ultraviolet (UV) light has been used in some settings to disinfect and sanitize surfaces. In some examples, multiple UV emitters are provided and powered by a relatively low power supply, such as 12 watts. While such UV devices offer promise in their ability to render inactive and/or kill certain pathogens, challenges exist in developing devices and systems for more effective delivery of such UV radiation.

SUMMARY

According to one aspect, an ultraviolet (UV) light-emitting assembly is provided that comprises a plurality of UV light emitters, a first UV light emitter support seating the plurality of UV light emitters, and a second UV light emitter support seating the plurality of UV light emitters. The first UV light emitter support is spaced by a gap from the second UV light emitter support. A first heat sink is affixed to the first UV light emitter support and a second heat sink affixed to the second UV light emitter support. A thermally conductive and electrically insulating plate contacts the first heat sink and the second heat sink.

According to another aspect, an ultraviolet (UV) light-emitting assembly is provided that comprises a plurality of UV light emitters, a first UV light emitter support seating the plurality of UV light emitters, and a second UV light emitter support seating the plurality of UV light emitters. The first UV light emitter support is spaced by a gap from the second UV light emitter support. A moving mechanism is configured to vary the gap between the first UV light emitter support and the second UV light emitter support to thereby change an intensity of UV light emitted from the plurality of UV light emitters.

According to another aspect, an ultraviolet (UV) light-emitting assembly is provided that comprises a plurality of UV light emitters, a first UV light emitter support seating the plurality of UV light emitters, and a second UV light emitter support seating the plurality of UV light emitters. The first UV light emitter support is spaced from the second UV light emitter support. The assembly further includes a heat sink comprising an actively-cooled plate. A first thermally conductive and electrically insulating pad comprises a first upper face that contacts a first bottom face of the first UV light emitter support and a first lower face that contacts the actively-cooled plate. A second thermally conductive and electrically insulating pad comprises a second upper face that contacts a second bottom face of the second UV light emitter support and a second lower face that contacts the actively-cooled plate.

According to another aspect, a method for varying UV intensity emitted by a plurality of UV light emitters is provided. The method is performed using a first UV light emitter support seating the plurality of UV light emitters and a second UV light emitter support seating the plurality of UV light emitters, wherein the first UV light emitter support is spaced from the second UV light emitter support. The method includes energizing the plurality of UV light emitters to emit a first UV light intensity when the first UV light emitter support is spaced from the second UV light emitter support by a first gap. The method includes moving the first UV light emitter support away from the second UV light emitter support until the first UV light emitter support is spaced from the second UV light emitter support by a second gap greater than the first gap. The method further includes energizing the plurality of UV light emitters to emit a second UV light intensity greater than the first UV light intensity when the first UV light emitter support is spaced from the second UV light emitter support by a second gap.

DETAILED DESCRIPTION

In view of the considerations discussed above, FIGS. 1 and 2 show one example of a system for disinfecting one or more components using ultraviolet (UV) light-emitting assemblies of the present disclosure. As described in more detail below, in some examples the system utilizes UV light-emitting assemblies incorporating one or more heat sinks that provide heat transfer functionality to enable the assemblies to operate at higher power and provide correspondingly higher UV irradiation. In some examples described below, the assemblies may be mechanically controlled to vary the UV light intensity emitted by the UV light emitters.

Figure 1:
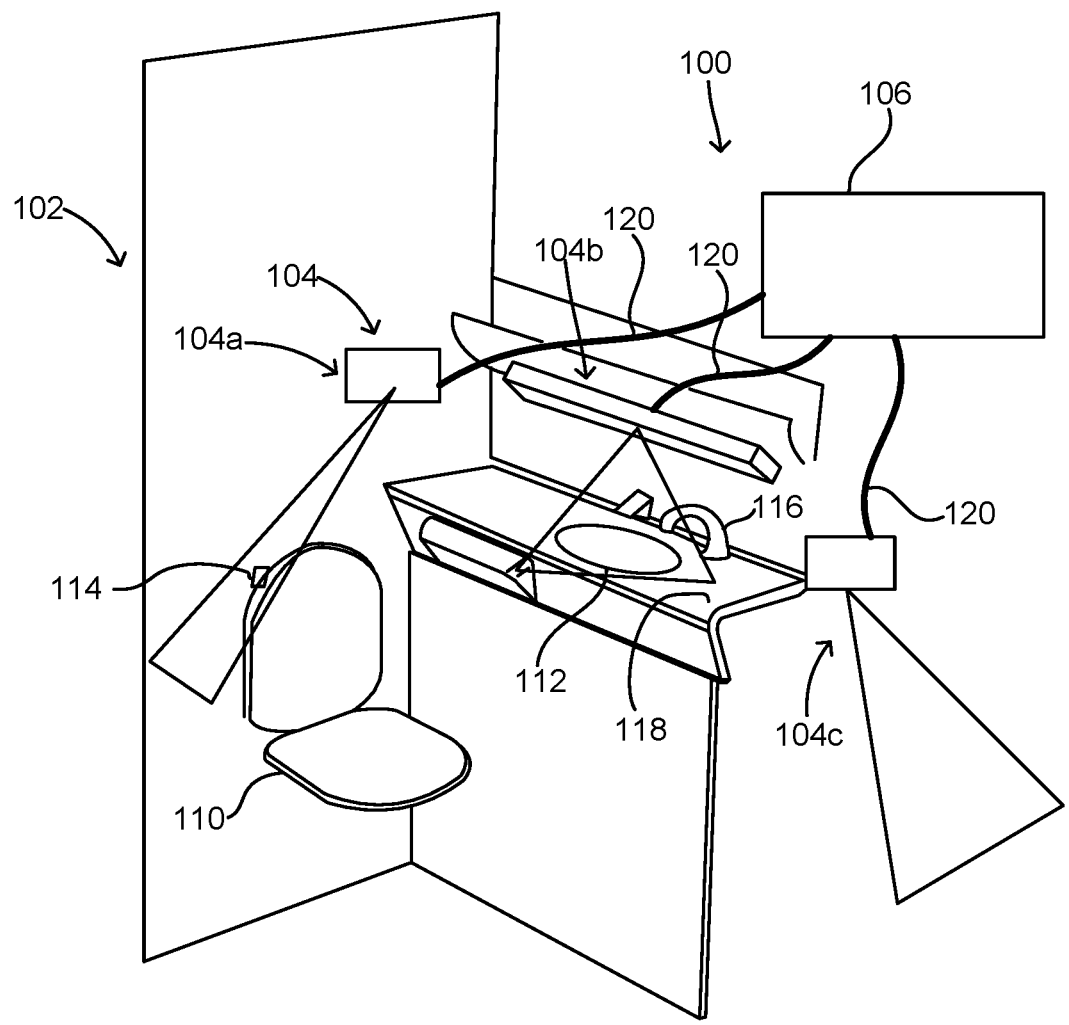
FIG. 1 shows a perspective view of a disinfecting system within a lavatory according to examples of the present disclosure.

FIG. 1 illustrates a perspective view of a lavatory 102 that includes a system 100 for disinfecting one or more components using ultraviolet (UV) light. The system 100 includes a plurality of UV light-emitting modules 104 containing UV light-emitting assemblies as described further below.

In the example of FIG. 1, three UV light-emitting modules 104a, 104b, and 104c are shown. The system 100 also includes a power supply module 106 that is electrically connected to each of the UV light-emitting modules 104 and provides power to the UV light-emitting assemblies inside the modules to generate UV light for disinfecting and/or sanitizing components and their surfaces in the lavatory 102.

In other examples, the system 100 utilizes fewer or more than three UV light-emitting modules 104 that are electrically connected to the power supply module 106. In still other examples, the system 100 and/or individually powered UV light-emitting modules 104 can be utilized in a variety of environments, including but not limited to kitchens, galleys, retail establishments, medical facilities, arenas, places of worship, banquet halls, theatres, concert venues, commercial businesses, factories, and other spaces. In some examples, the system 100 and/or individually powered UV light-emitting modules 104 can be utilized in aircraft, spacecraft, and other vehicles, such as buses, trains, marine vessels, and the like.

Figure 15:
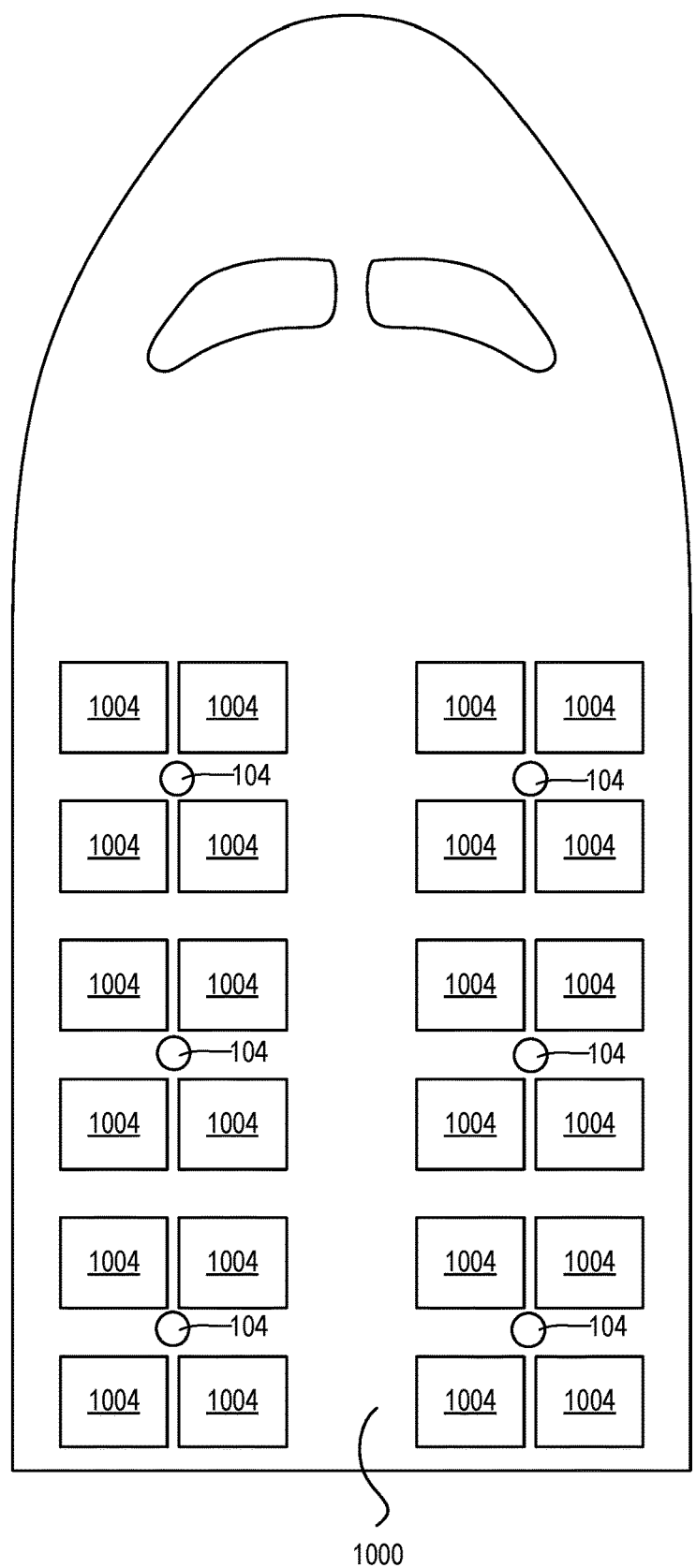
FIG. 15 depicts an aircraft environment in which UV light-emitting assemblies of the present disclosure are installed.

In a commercial aircraft, the system 100 can be located within a cabin, galley, crew rest area, assembly area, cargo area, flight deck, lavatory, and other areas in which individuals, passengers, flight crew, ground crew, and/or maintenance personnel may be located. In the present example of FIG. 1, the lavatory 102 can be located within a vehicle, such as within a cabin of a commercial aircraft. For example, FIG. 15 depicts an aircraft environment in which UV light-emitting modules 104 are installed above passenger seats 1004 in the cabin 1000 of the aircraft.

Figure 2:
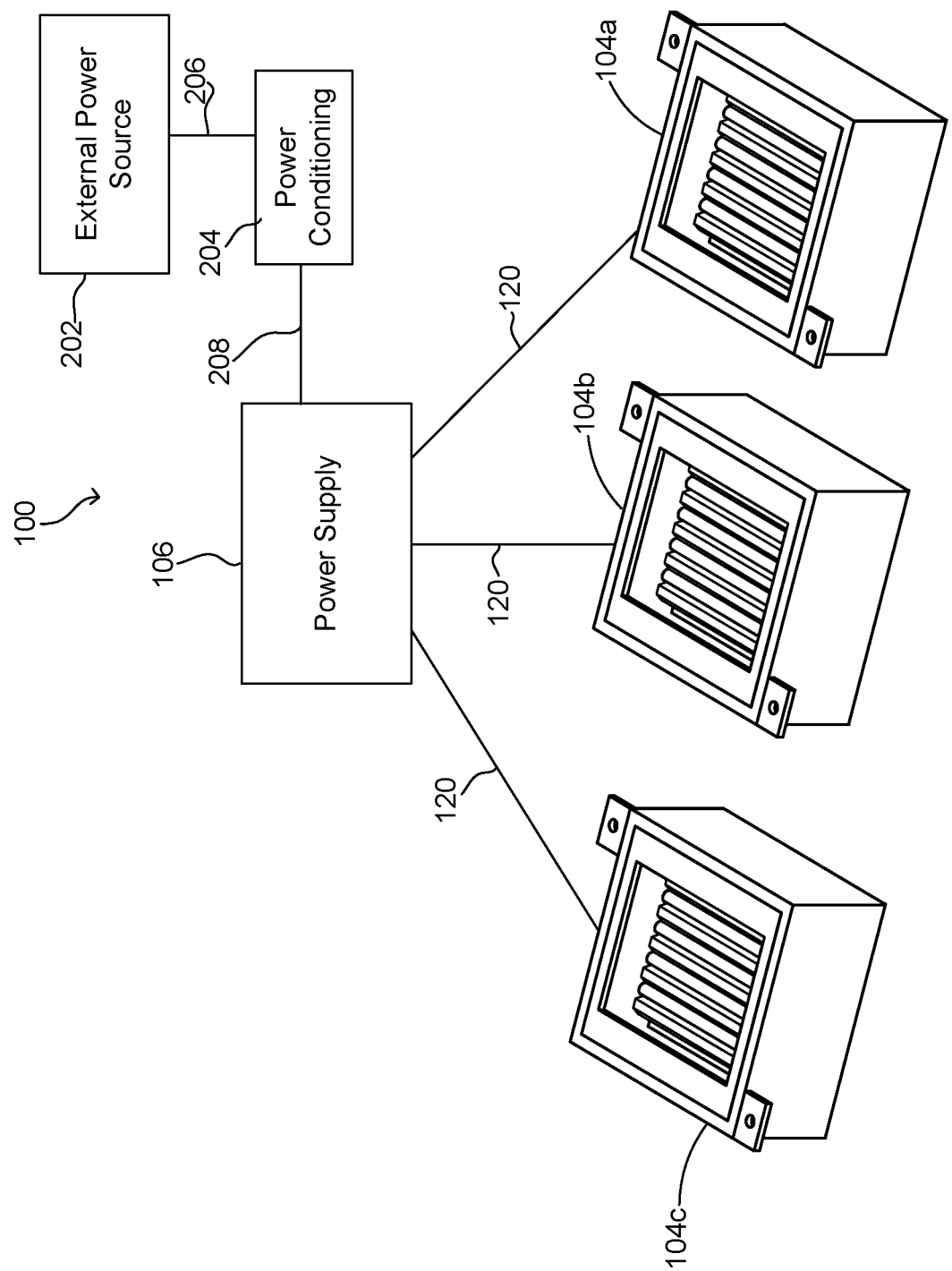
FIG. 2 shows a schematic diagram of the disinfecting system of FIG. 1 according to examples of the present disclosure.
Figure 3:
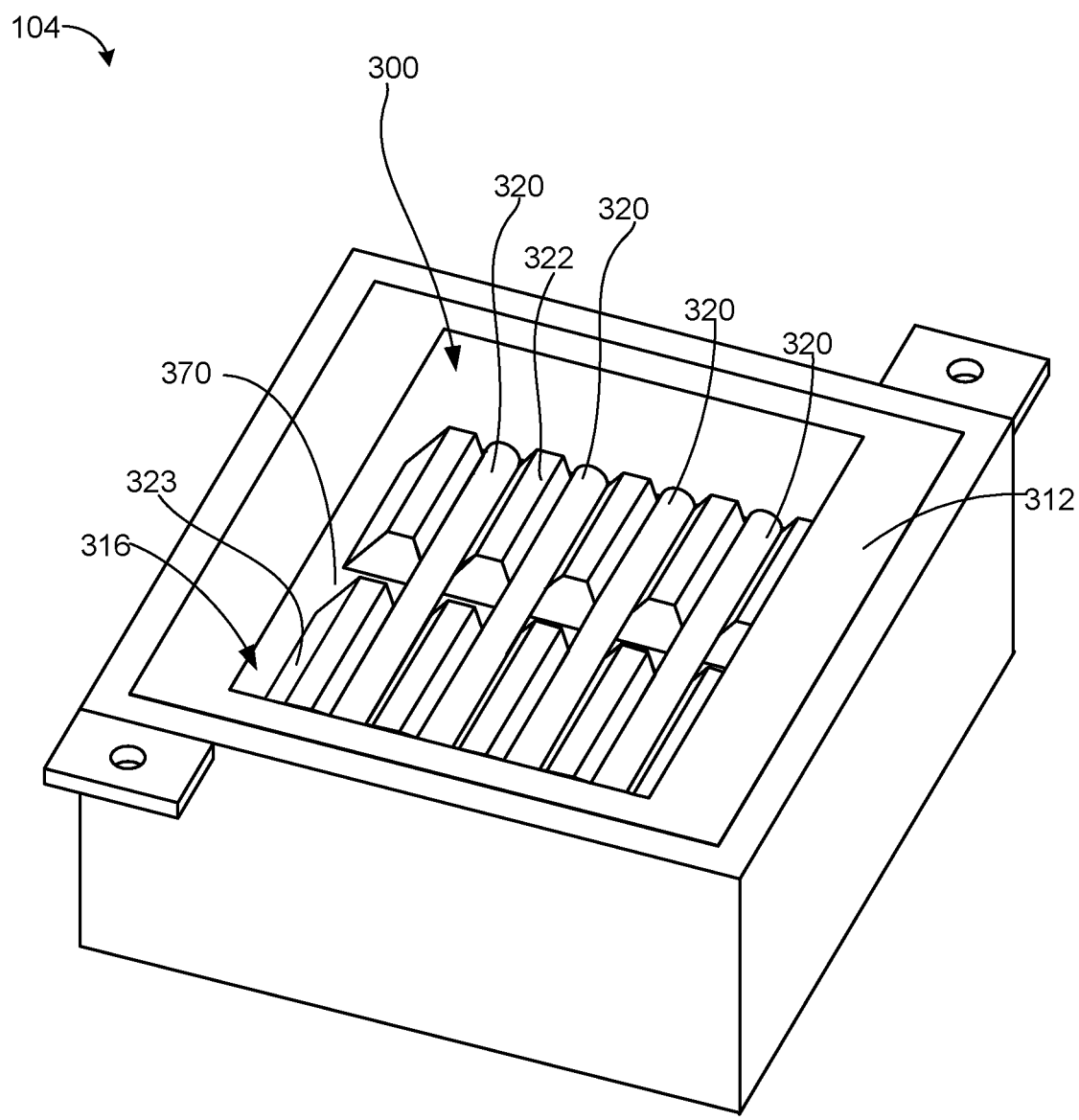
FIG. 3 shows one example of an ultraviolet (UV) light-emitting assembly housed in a module according to examples of the present disclosure.

FIGS. 2 and 3 illustrate one example of a module 104 in which UV light-emitting assemblies of the present disclosure may be enclosed. Module 104 is provided merely as one example, and any suitable housing or enclosure may be utilized with the UV light-emitting assemblies described herein. In other examples, one or more UV light-emitting assemblies may be utilized in a portable device, such as a wand, that is configured to be held by a user. In some examples, such a portable device is also configured to be removably mounted to a support structure, such as a wall.

Returning to the example of FIG. 1, the UV light-emitting modules 104 are positioned to emit the UV light towards one or more components within the lavatory 102 for disinfecting and/or sanitizing the components. In the illustrated example, the one or more components include a sink 112 and a toilet 110. In this example, the UV light-emitting modules 104 are positioned to emit UV light towards different components. For example, the first UV light-emitting module 104a is positioned to emit UV light towards the toilet 110 including a flush actuator 114 (e.g., lever, button, etc.) of the toilet 110. The second UV light-emitting module 104b is positioned to emit UV light towards the sink 112 and the surrounding region, such as portions of the faucet 116 and countertop 118. The third UV light-emitting module 104c is positioned to emit UV light towards the door (not shown) used to enter and exit the lavatory 102.

In some examples, two or more UV light-emitting modules 104 are positioned to emit UV light towards a common component. In some examples, two or more UV light-emitting modules 104 are physically adjacent and/or mechanically coupled to one another.

The power supply module 106 is electrically connected to the UV light-emitting modules 104 to provide power to the UV light-emitting assemblies therein. In some examples the power supply module 106 includes processing and/or power modulation circuitry within an enclosure or housing. In different examples the power supply module 106 receives electrical energy from a power source, such as power distribution panel or a battery, and distributes the electrical energy among the UV light-emitting modules 104.

In the example of FIG. 1, the power supply module 106 is mounted within the lavatory 102 and is electrically connected to the UV light-emitting modules 104 via respective power leads 120, such as one or more electrical wires or power cables. In other examples, one or more of the UV light-emitting modules 104 are integrated with the power supply module 106 in a common housing.

FIG. 2 illustrates a schematic block diagram of the system 100 according to an example of the present disclosure. In this example, the power supply module 106 receives electrical energy from an external power source 202 that is separate and discrete from the power supply module 106. In some examples the power source 202 is a vehicle electrical system onboard a vehicle or an electrical system of a building or facility. In other examples, the power source 202 is a battery, a generator, or the like.

In the present example the power supply module 106 is electrically connected to the external power source 202 via a power conditioning circuit 204 and power cables 206 and 208. In different examples the power conditioning circuit 204 includes one or more rectifiers, power factor correction circuits, and/or capacitors for electromagnetic interference filtering. In other examples, the power conditioning circuit 204 is integrated with the power supply module 106 in a common enclosure, such as a housing of the power supply module.

In this example, the power supply module 106 receives electrical energy from the power conditioning circuit 204 and controls distribution of the electrical energy among the UV light-emitting modules 104. In this example, the power conditioning circuit 204 receives alternating current (AC) electrical energy from the external power source 202 and converts the AC electrical energy to DC electrical energy. This DC electrical energy is supplied to the power supply module 106, which converts the DC electrical energy to AC electrical energy and supplies the AC to the UV light-emitting modules 104 to power the generation of UV light as described in more detail below. In some examples, the power supply module 106 also controls one or more operations of the UV light-emitting modules 104, such as activating and deactivating the modules, and modulating the power output of the modules.

Additionally, and as described in more detail below, some examples of UV light-emitting assemblies of the present disclosure utilize one or more heat sinks that enable the modules to operate at higher power and provide correspondingly higher UV irradiation than prior UV emitters. Additionally, and in some examples described below, one or more moving mechanisms are utilized to vary the UV light intensity emitted by the UV light emitters of an assembly.

With reference now to FIGS. 3-6, one example of a UV light-emitting assembly 300 according to the present disclosure is illustrated. In different use case examples, the UV light-emitting assembly 300 can be enclosed in module 104 described above and shown in FIG. 3, or in a variety of other housings, enclosures, or portable devices. In different use cases, the UV light-emitting assembly 300 and the other examples of UV light-emitting assemblies described herein can be utilized in a UV disinfecting system, such as system 100, and/or in standalone devices.

As shown in FIG. 3, in this example the UV light-emitting assembly 300 is housed in module 104 that comprises a face plate 312 including a light-transmitting aperture 316 through which UV light from one or more UV light emitters within the enclosure is transmitted. In different examples, the walls of the module 104 can be fabricated from a plastic material or from a conductive material, such as aluminum. In this example, the UV light-emitting assembly 300 utilizes four UV light emitters 320. In other examples, fewer or more than four UV light emitters may be utilized in UV light-emitting assemblies according to the present disclosure.

The plurality of UV light emitters 320 is configured to emit 222 nm wavelength UV light. In some examples, the UV light emitters 320 can be excimer lamps that utilize a krypton-chlorine (Kr—Cl) gas mixture provided in the lamp bulb. Such excimer lamps emit UV light having a wavelength of 222 nm that can disinfect and sanitize component surfaces via localized anti-viral and antimicrobial effects. Further, 222 nm wavelength UV light can disinfect and sanitize surfaces without skin damaging effects associated with conventional germicidal ultraviolet (UV) exposure. In other examples, the UV light-emitting assembly 300 can utilize other types of UV emitters and UV lamps. Additionally, and as described in more detail below, the UV light emitters 320 are seated in one or more UV light emitter supports within the module 104.

As noted above, in the example of FIGS. 3-6 the UV light emitters 320 are seated in V-shaped grooves in a first UV light emitter support 322 and a second UV light emitter support 323 that extend parallel to one another. In some examples, the UV light emitter supports 322, 323 are fabricated from a conductive material, such as aluminum. In this manner and by seating the UV light emitters 320 in the supports, the emitters are electrically coupled to the supports.

Figure 4:
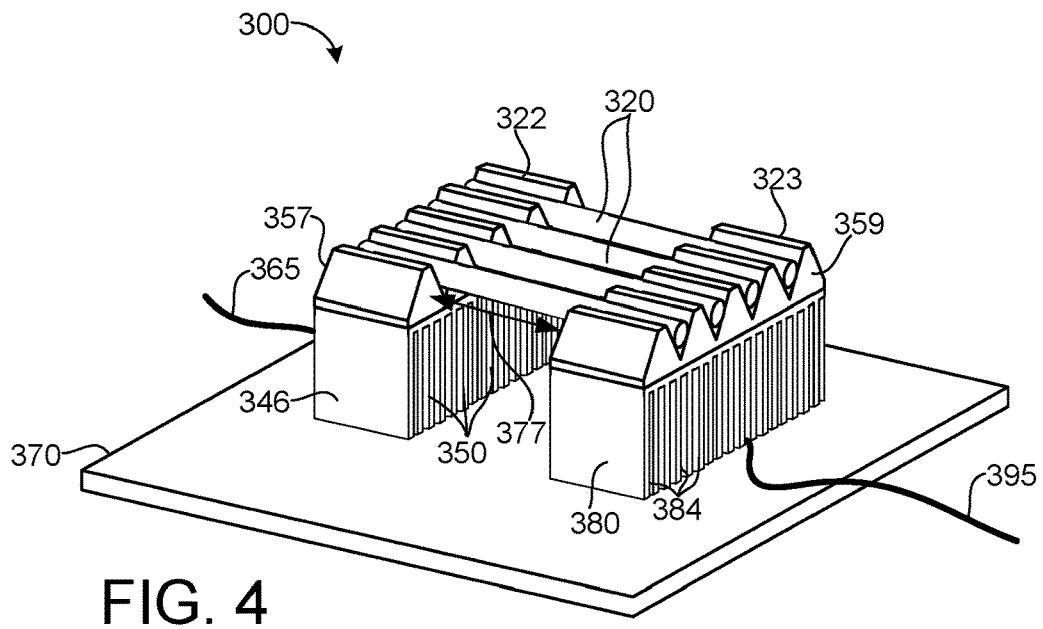
FIG. 4 shows one example of a UV light-emitting assembly according to examples of the present disclosure.
Figure 5:
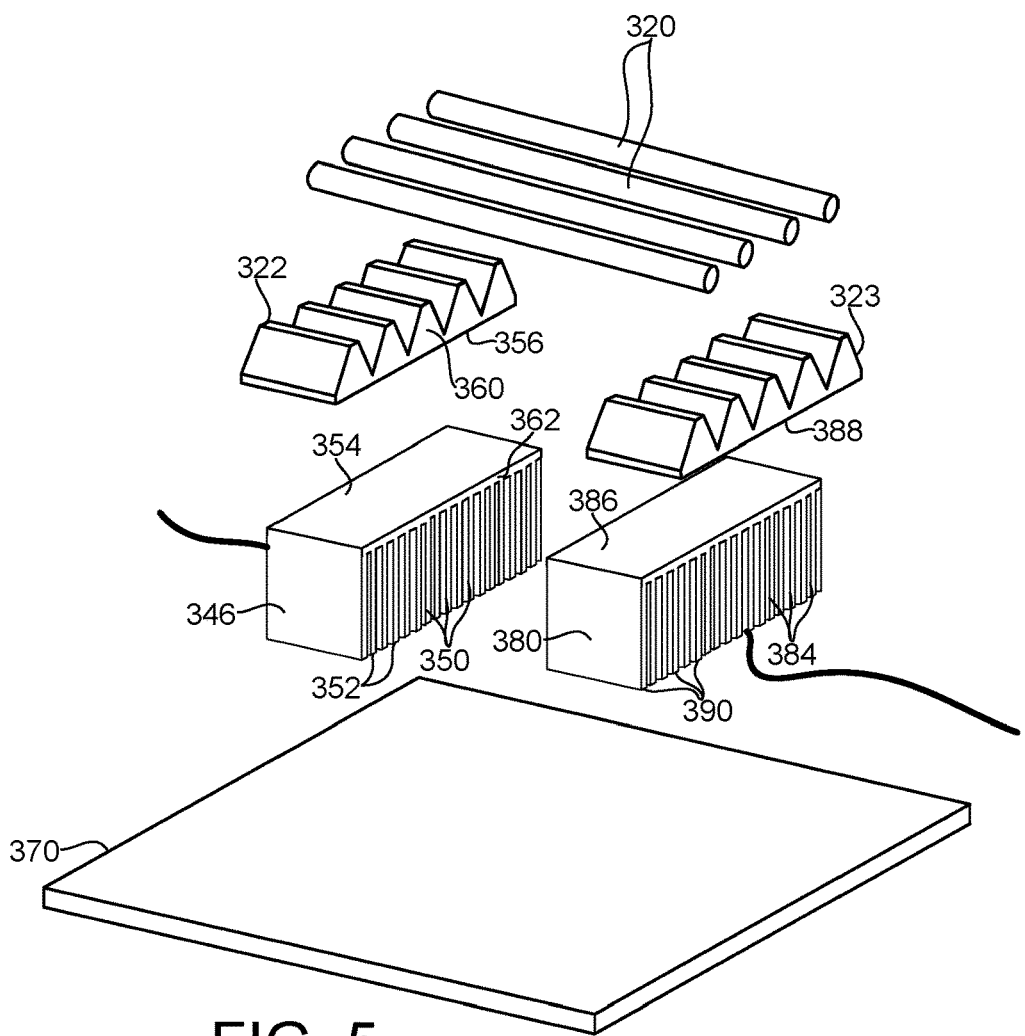
FIG. 5 shows an exploded view of the UV light-emitting assembly of FIG. 4.
Figure 6:
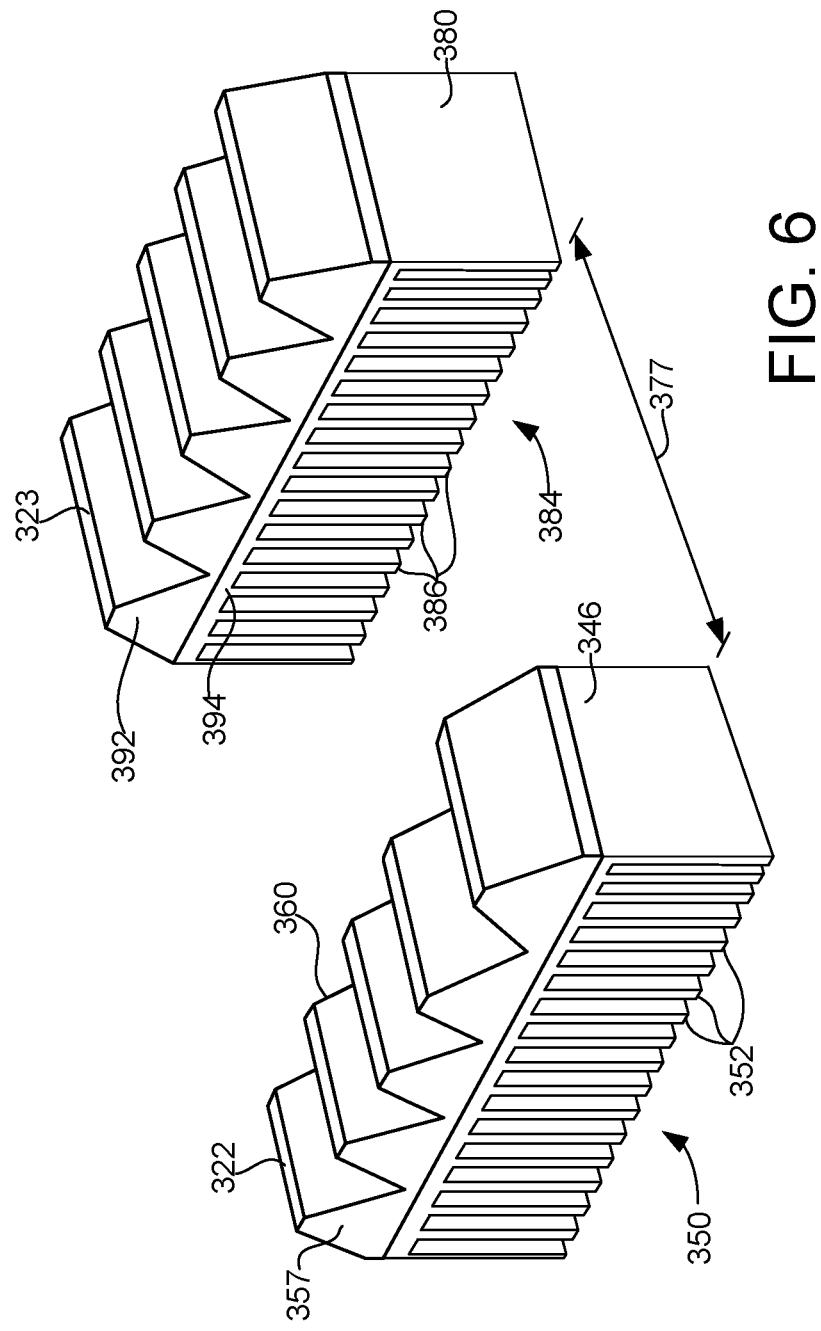
FIG. 6 shows another view of the UV light emitter supports and heat sinks of FIG. 4 according to examples of the present disclosure.

With reference to FIGS. 4-6 showing light-emitting assembly 300, and in one potential advantage of the present disclosure, in this example a first heat sink 346 is affixed to the first UV light emitter support 322 and a second heat sink 380 is affixed to the second UV light emitter support 323. Accordingly, and as descried in more detail below, heat sinks 346 and 380 provide heat transfer functionality that enables the assembly 300 to operate at higher powers and provide correspondingly higher UV irradiation. In some examples, such higher power enabled by heat sinks 346 and 380 in combination with increased gaps between the UV light emitter supports 322, 323 generates significantly increased UV light intensity and larger irradiance areas as compared to prior configurations. In this manner, fewer UV light assemblies may be utilized to sterilize a given area.

In this example, the first heat sink 346 comprises a first plurality of fins 350 extending from a first base portion 354 of the first heat sink. The first base portion is affixed to a first bottom face 356 of the first UV light emitter support 322. Similarly, the second heat sink 380 comprises a second plurality of fins 384 extending from a second base portion 386 of the second heat sink. The second base portion 386 is affixed to a second bottom face 388 of the second UV light emitter support 323.

In the present example, the UV light emitter supports and heat sinks are separate components that are affixed to one another. In other examples of a heat sink being "affixed" to a UV light emitter support, the heat sink and UV light emitter support are produced from a single material source or material, such as via metalworking or additive manufacturing.

With reference also to FIG. 6, each fin 350 of the first plurality of fins comprises a first distal end 352 opposite to the first base portion 354, and these first distal ends are contacting a thermally conductive and electrically insulating plate 370. Similarly, each fin 384 of the second plurality of fins comprises a second distal end 390 opposite to the second base portion 386, with these second distal ends also contacting the thermally conductive and electrically insulating plate 370. In some examples, the thermally conductive and electrically insulating plate 370 is fabricated from a fluoropolymer material, such as polytetrafluoroethylene (PTFE). Accordingly, in these examples the thermal conductivity of the plate 370 further facilitates heat transfer from the UV light emitter supports 322, 323 via first heat sink 346 and second heat sink 380 to cool the UV light emitters 320. Additionally, fluoropolymer materials have properties that reflect 222 nm UV light. Accordingly, this configuration also provides a larger surface area of 222 nm UV light reflective material from which UV light emitted by the UV light emitters 320 is reflected.

Additionally, the gap 377 between first UV light emitter support 322 and second UV light emitter support 323 (and correspondingly between first heat sink 346 and second heat sink 380) can be widened to maximize the amount of gas mixture in the light emitter bulbs that is excited, and thereby increase the emitted UV light. In one example and with reference to FIG. 4, the first UV light emitter support 322 and second UV light emitter support 323 (and first heat sink 346 and second heat sink 380) are positioned with a gap 377 that places both ends of each of the UV light emitters 320 substantially flush with the first outer side 357 and the second outer side 359 of the UV light emitter support 322, 323, respectively.

In some examples, the gap 377 between first UV light emitter support 322 and second UV light emitter support 323 can be significantly wider than in prior configurations. In one example, the gap 377 is approximately 17 mm. In this example and where the power supplied to the UV light-emitting assembly 300 is 100 W, the assembly generates approximately 9 mW/cm$^2$ over approximately 29.4 cm$^2$. By comparison, this example area irradiated by UV light is approximately 29% larger than the area irradiated by the same components configured with a 6 mm gap between first UV light emitter support 322 and second UV light emitter support 323. Advantageously, utilizing such an increased gap coupled with the heat dissipation functionality of the present configurations enables these configurations to utilize increased power supplies to provide more effective delivery of UV radiation to wider surface areas. In other examples and in other configurations, gaps between the first UV light emitter support 322 and second UV light emitter support 323 can be greater than 17 mm.

With reference to FIGS. 5 and 6, the first UV light emitter support 322 comprises a first inner support face 360 that faces a second inner support face 392 of the second UV light emitter support 323. Similarly, the first heat sink 346 comprises a first inner heat sink face 362 (including inner surfaces of the fins 350) that faces a second inner heat sink face 394 (including inner surfaces of the fins 384) of the second heat sink 380. As shown in FIGS. 4 and 6, the first inner support face 360 is substantially flush with the first inner heat sink face 362, and the second inner support face 392 is substantially flush with the second inner heat sink face 394. Advantageously, and particularly as power to the UV light emitter supports 322, 323 is increased, this configuration prevents electrical arcing between the first heat sink 346 and second heat sink 380.

In examples where the UV light emitter supports 322, 323 are fabricated from a conductive material, such as aluminum, the supports are electrically coupled to a power source via lead wires 365 and 395, respectively. In some examples the power source is the power supply module 106 of system 100.

In other examples, the UV light emitter supports 322, 323 can be fabricated from a fluoropolymer, such as polytetrafluoroethylene (PTFE). In these examples, the UV light emitters 320 are directly coupled to a power source via lead wires connected to terminals at each end of the of the emitters.

Figure 7:
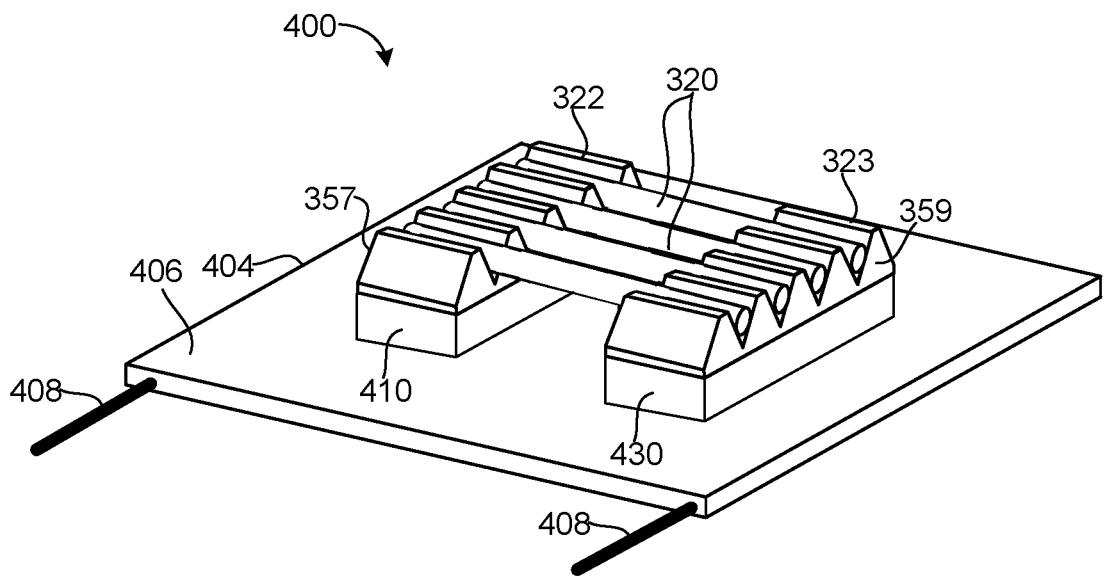
FIG. 7 shows another example of a UV light-emitting assembly according to examples of the present disclosure.
Figure 8:
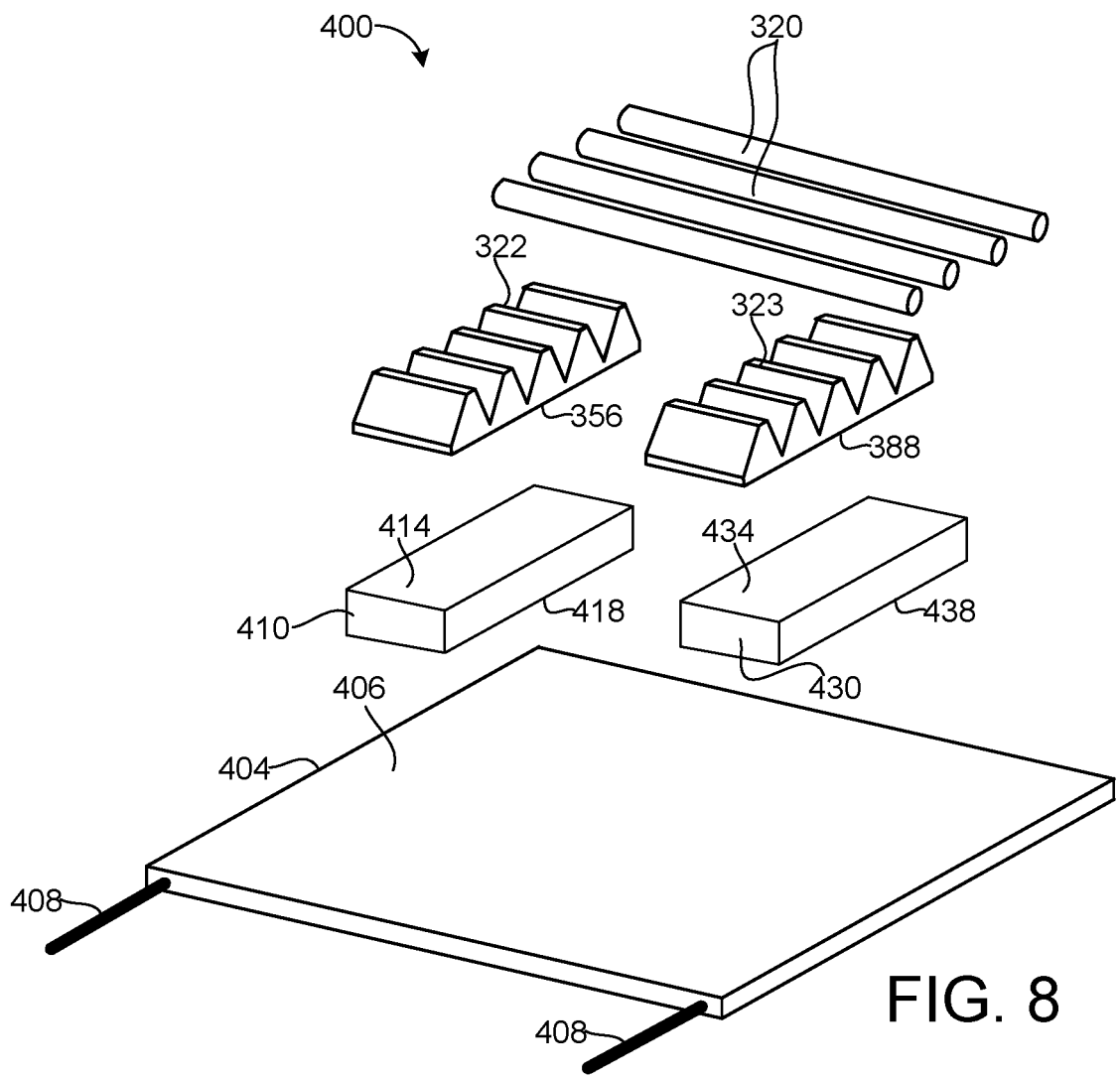
FIG. 8 shows an exploded view of the UV light-emitting assembly of FIG. 7.
Figure 9:
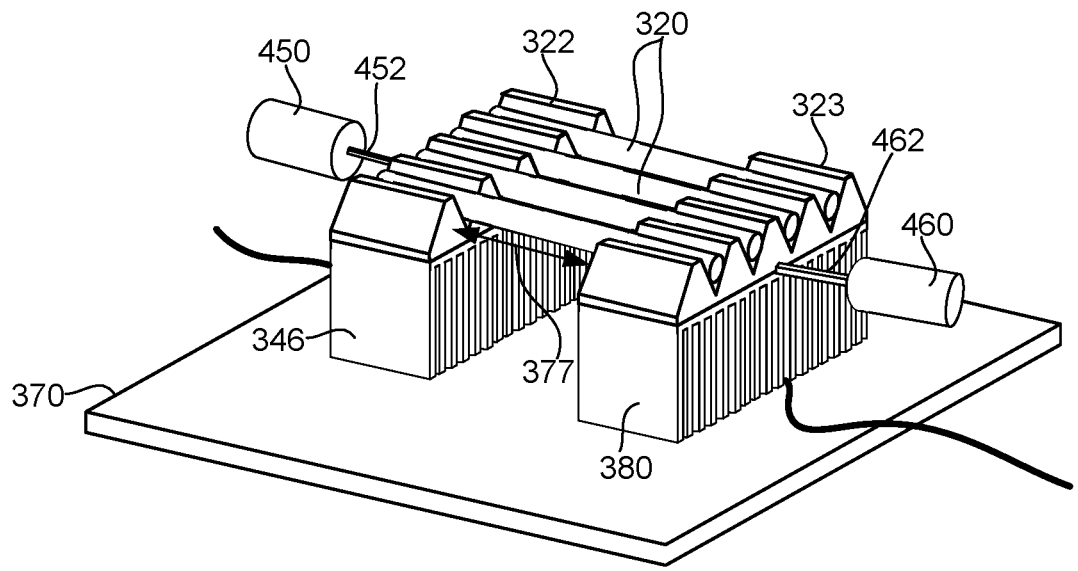
FIG. 9 shows another example of a UV light-emitting assembly including a moving mechanism according to examples of the present disclosure.

With reference now to FIGS. 7-9, in some examples a UV light-emitting assembly 400 of the present disclosure utilizes a heat sink in the form of an actively-cooled plate 404. In one example, the actively-cooled plate 404 is fabricated from a thermally-conductive material, such as aluminum, and includes embedded tubing 408 through which liquid coolant is circulated. In different examples, a variety of materials, heat-exchanging technologies, and configurations can be utilized for the actively-cooled plate 404.

In these examples, thermally conductive and electrically insulating pads are located between the UV light-emitting supports and the actively-cooled plate 404. As shown in FIGS. 7 and 8, a first thermally conductive and electrically insulating pad 410 includes a first upper face 414 that contacts and is affixed to the first bottom face 356 of first UV light-emitting support 322. The first thermally conductive and electrically insulating pad 410 also includes a first lower face 418 that contacts an upper surface 406 of the actively-cooled plate 404. Similarly, a second thermally conductive and electrically insulating pad 430 includes a second upper face 434 that contacts and is affixed to the second bottom face 388 of second UV light-emitting support 322, and a second lower face 438 that contacts the upper surface 406 of the actively-cooled plate 404.

In this example, the actively-cooled plate 404 in combination with the first and second thermally conductive and electrically insulating pads 410, 430 operates to transfer heat from the first and second UV light-emitting supports 322, 323. Additionally, and as described above, the gap between first UV light emitter support 322 and second UV light emitter support 323 can be widened to maximize the amount of gas mixture in the light emitter bulbs that is excited, and thereby increase the emitted UV light. In this respect and as shown in FIG. 7, the first UV light emitter support 322 and second UV light emitter support 323 are spaced apart to create a gap that places both ends of each of the UV light emitters 320 substantially flush with the first outer side 357 and the second outer side 359 of the UV light emitter support 322, 323, respectively.

The aluminum UV light emitter supports 322, 323 can be electrically coupled to a power source in any suitable manner. In other examples, the UV light emitters 320 are directly coupled to a power source via lead wires connected to terminals at each end of the of the emitters.

In other examples, the UV light emitter supports 322, 323 can be fabricated from a fluoropolymer, such as polytetrafluoroethylene (PTFE). In these examples, the UV light emitters 320 are directly coupled to a power source via lead wires connected to terminals at each end of the of the emitters.

In some examples, assemblies of the present disclosure also are configured to enable real-time variation of the gap between the first UV light emitter support 322 and the second UV light emitter support 323, and thereby vary the UV light intensity of UV light emitted from the UV light emitters. With reference now to FIG. 9, in this example the UV light-emitting assembly 300 of FIGS. 4 and 5 also comprises a moving mechanism in the form of a first actuator 450 and second actuator 460. In this example moving mechanism and as described in more detail below, the first actuator 450 and second actuator 460 are configured to translate the first heat sink 346 and the second heat sink 380, respectively, relative to the thermally conductive and electrically insulating plate 370.

In this example, the first actuator 450 includes a first rod 452 that is coupled to the first light emitter support 322. The first actuator 450 is controlled to translate the first light emitter support 322 and attached first heat sink 346 in a positive and negative x-axis direction. Similarly, the second actuator 460 includes a second rod 462 that is coupled to the second light emitter support 323. The second actuator 460 is also controlled to translate the second light emitter support 323 and attached second heat sink 380 in a positive and negative x-axis direction.

Figure 10:
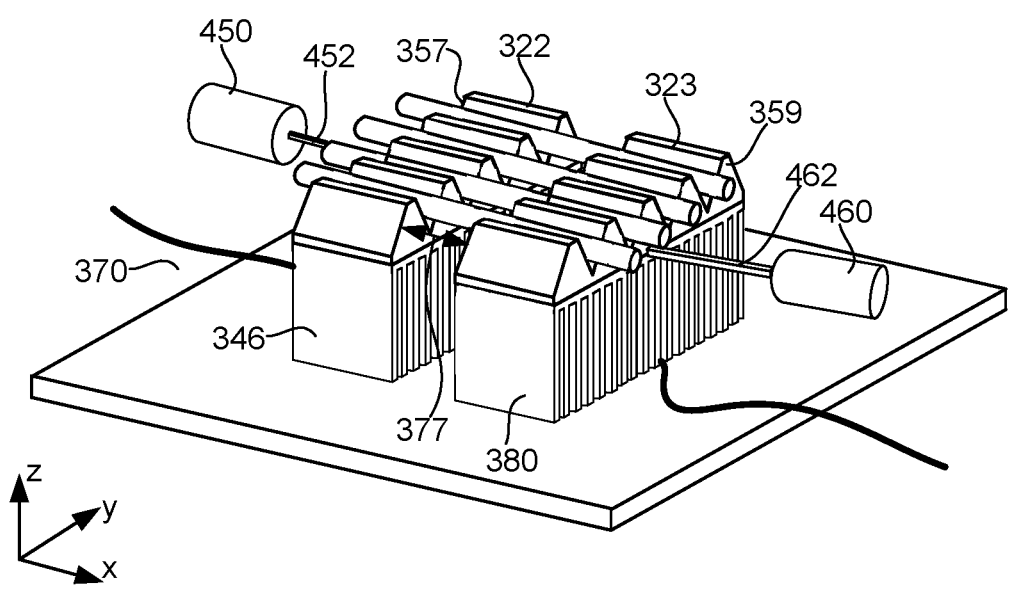
FIG. 10 shows the UV light-emitting assembly of FIG. 9 with the UV light emitter supports and heat sinks moved closer to one another.

In this manner and in one example shown in FIGS. 9 and 10, the first actuator 450 is controlled to translate the first UV light emitter support 322 and first heat sink 346 in a positive x-axis direction, and the second actuator 460 is controlled translate the second UV light emitter support 323 and second heat sink 380 in a negative x-axis direction to narrow the gap 377 between the two UV light emitter supports and heat sinks. As the first and second UV light emitter supports 322, 323 are moved, they slide underneath the UV light emitters 320 such that the ends of the emitters protrude beyond the first outer side 357 and second outer side 359 of the UV light emitter support 322, 323, respectively, as shown in FIG. 10.

With the gap 377 narrowed between the first and second UV light emitter supports 322, 323, the distance between electrical coupling locations on each UV light emitter 320 is also narrowed. In this manner, less of the gas mixture in the light emitter bulbs is excited, and the emitted UV light is reduced as compared to the wider gap 377 of FIG. 9. The frequency, voltage and/or other characteristics of the power supplied to the first and second UV light emitter supports 322, 323 also can be adjusted to vary the intensity of emitted UV light. In other examples and in different use cases, the first actuator 450 and/or second actuator 460 can be controlled to widen or narrow the gap between the two UV light emitter supports and heat sinks to thereby vary the UV light intensity of UV light emitted from the UV light emitters as desired.

Figure 11:
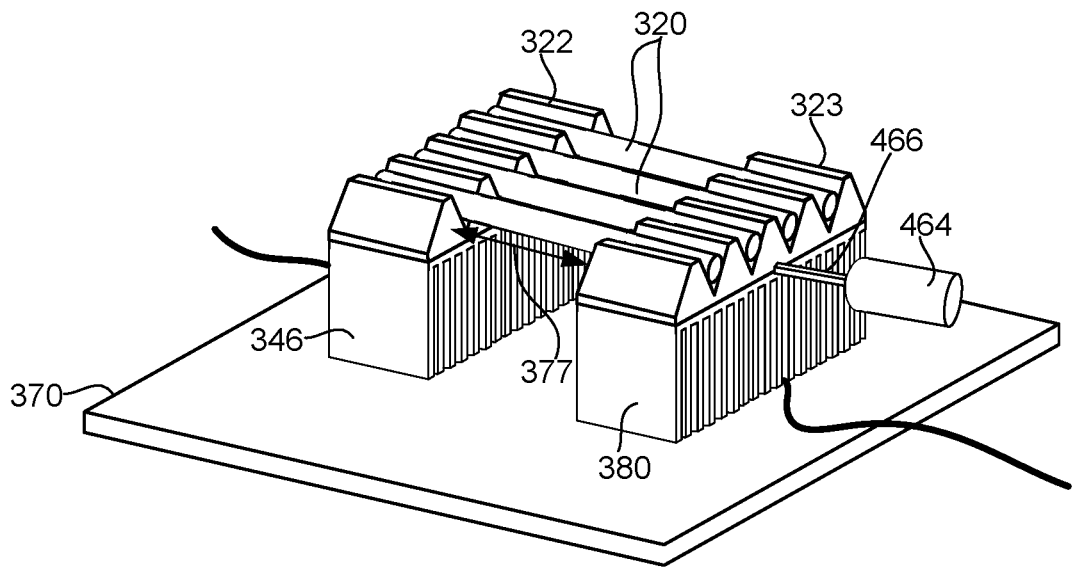
FIG. 11 shows another example of a UV light-emitting assembly including a moving mechanism according to examples of the present disclosure.
Figure 12:
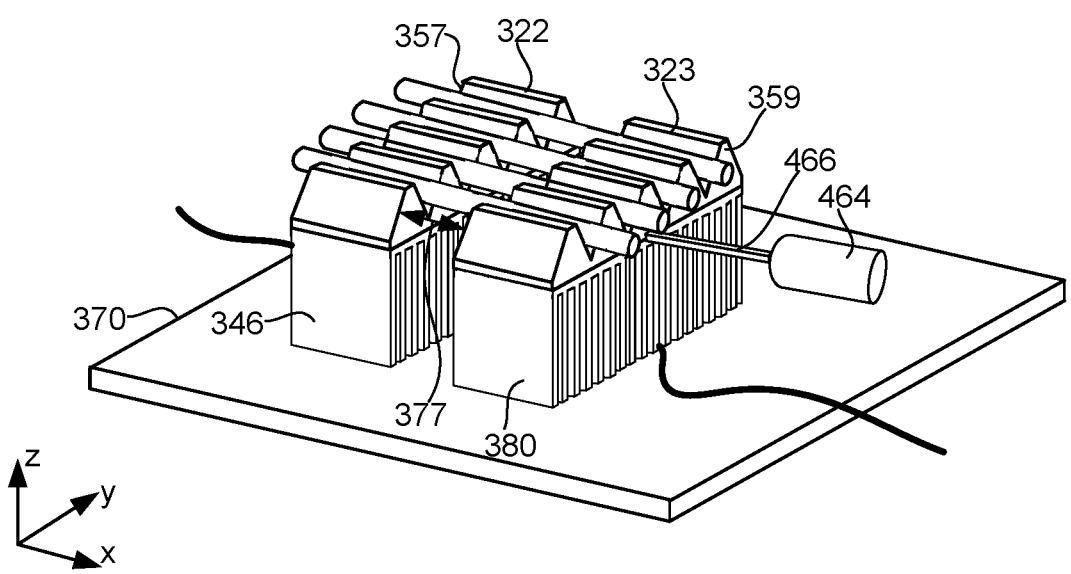
FIG. 12 shows the UV light-emitting assembly of FIG. 11 with one UV light emitter support and heat sink moved closer to the other.

In some examples, the moving mechanism is configured to translate only the first UV light emitter support 322 or the second UV light emitter support 323. With reference now to FIGS. 11 and 12, in this example a single actuator 464 is configured to extend and retract rod 466 to translate the second UV light emitter support 323 toward and away from the first UV light emitter support 322 to vary the gap 377 as desired.

In different examples, the actuators described herein can be any suitable type of motion control component, including but not limited to servo motors, stepper motors, and solenoids. In other examples, any other suitable motion control or motion imparting components may be utilized to translate one or more of the UV light emitter supports, including but not limited to gearing mechanisms, chain drives, and belt drives.

Figure 13:
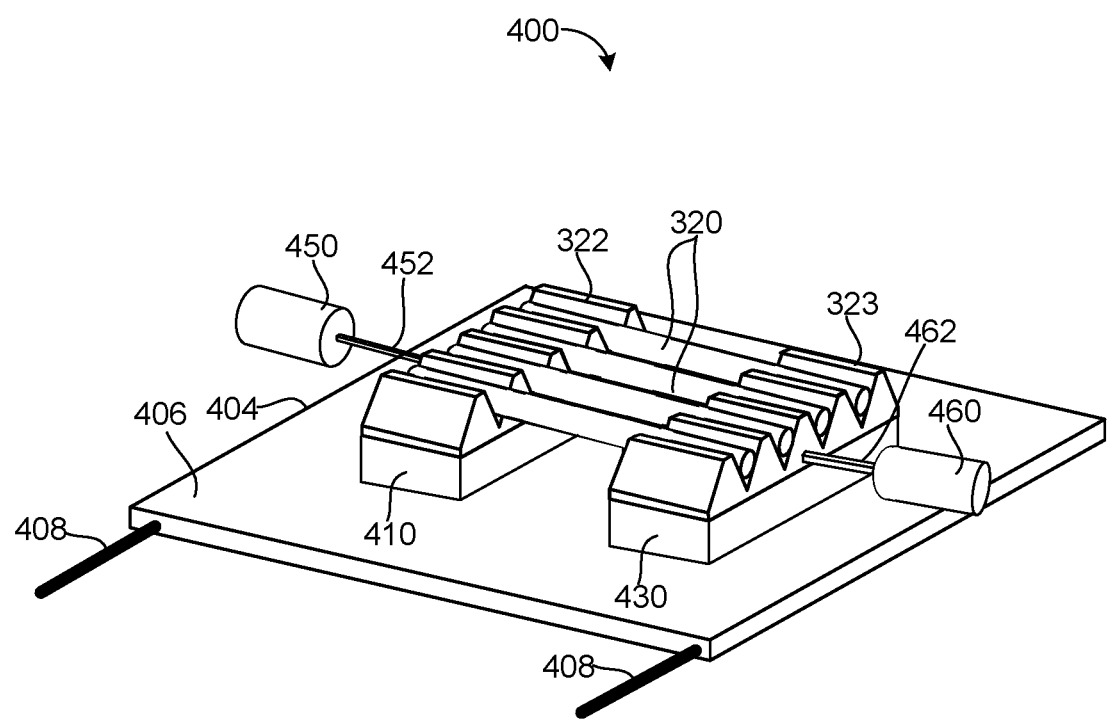
FIG. 13 shows another example of a UV light-emitting assembly including a moving mechanism according to examples of the present disclosure.

In another example and with reference now to FIG. 13, in this example the UV light-emitting assembly 400 of FIGS. 7 and 8 also comprises a moving mechanism in the form of first actuator 450 and second actuator 460. In this example the first actuator 450 is configured to translate the first UV light emitter support 322 and first thermally conductive and electrically insulating pad 410 relative to the actively-cooled plate 404, and the second actuator 460 is configured to translate the second UV light emitter support 323 and second thermally conductive and electrically insulating pad 430 relative to the actively-cooled plate. As described above with respect to FIGS. 9 and 10, moving the first and second UV light emitter supports 322, 323 underneath the UV light emitters 320 changes the distance between electrical coupling locations on each UV light emitter 320, and correspondingly changes the intensity of emitted UV light.

In different examples of UV light-emitting assemblies of the present disclosure, the assemblies can utilize any suitable combinations of features described herein, including but not limited to heat sink features, component materials, and moving mechanisms.

Figure 14:
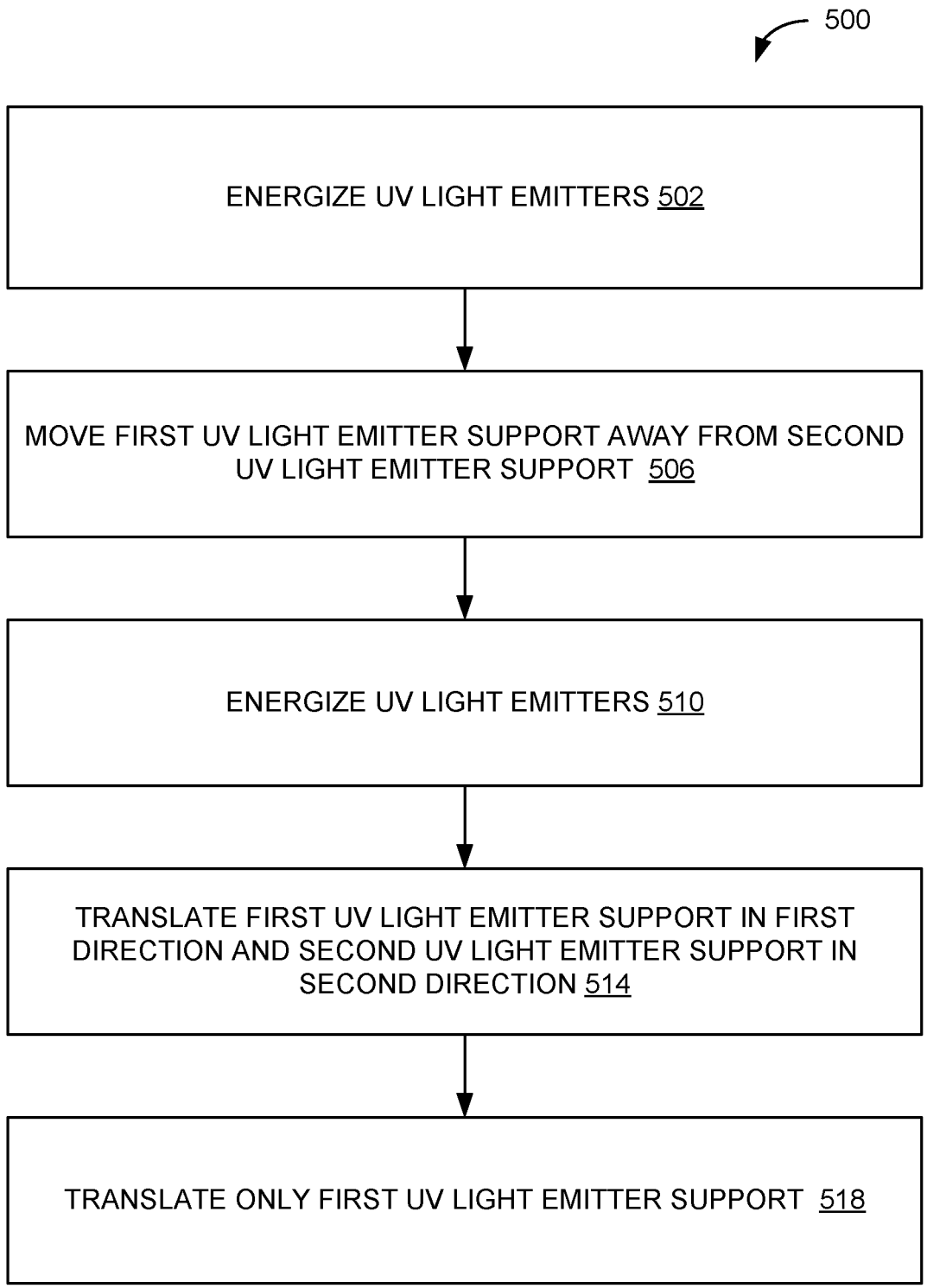
FIG. 14 shows a block diagram of an example method for varying UV light intensity emitted by a plurality of UV light emitters according to examples of the present disclosure.

Turning now to FIG. 14, a method 500 for varying UV light intensity emitted by a plurality of UV light emitters is illustrated. The method 500 is performed using a first UV light emitter support seating the plurality of UV light emitters and a second UV light emitter support seating the plurality of UV light emitters, wherein the first UV light emitter support is spaced from the second UV light emitter support.

At 502, method 500 includes the step of energizing the plurality of UV light emitters to emit a first UV light intensity when the first UV light emitter support is spaced from the second UV light emitter support by a first gap. At 506, the method 500 includes the step of moving the first UV light emitter support away from the second UV light emitter support until the first UV light emitter support is spaced from the second UV light emitter support by a second gap greater than the first gap. At 510, the method 500 includes energizing the plurality of UV light emitters to emit a second UV light intensity greater than the first UV light intensity when the first UV light emitter support is spaced from the second UV light emitter support by the second gap. At 514, the method 500 includes the step of translating the first UV light emitter support in a first direction and translating the second UV light emitter support in a second direction opposite to the first direction. At 518, the method 500 includes translating only the first UV light emitter support.

Further, the disclosure comprises configurations according to the following clauses.

Clause 1. An ultraviolet (UV) light-emitting assembly for disinfecting one or more components, the assembly comprising: a plurality of UV light emitters; a first UV light emitter support seating the plurality of UV light emitters; a second UV light emitter support seating the plurality of UV light emitters, wherein the first UV light emitter support is spaced from the second UV light emitter support; a first heat sink affixed to the first UV light emitter support; a second heat sink affixed to the second UV light emitter support; and a thermally conductive and electrically insulating plate contacting the first heat sink and the second heat sink.

Clause 2. The UV light-emitting assembly of clause 1, wherein the first heat sink comprises a first plurality of fins extending from a first base portion of the first heat sink, and the second heat sink comprises a second plurality of fins extending from a second base portion of the second heat sink.

Clause 3. The UV light-emitting assembly of clause 2, wherein the first base portion is affixed to a first bottom face of the first UV light emitter support, and the second base portion is affixed to a second bottom face of the second UV light emitter support.

Clause 4. The UV light-emitting assembly of clause 3, wherein each fin of the first plurality of fins comprises a first distal end opposite to the first base portion, and the first distal ends of the first plurality of fins are contacting the thermally conductive and electrically insulating plate, and wherein each fin of the second plurality of fins comprises a second distal end opposite to the second base portion, and the second distal ends of the second plurality of fins are contacting the thermally conductive and electrically insulating plate.

Clause 5. The UV light-emitting assembly of any of clauses 1-4, wherein the first UV light emitter support comprises a first inner support face that faces a second inner support face of the second UV light emitter support, the first heat sink comprises a first inner heat sink face that faces a second inner heat sink face of the second heat sink, wherein the first inner support face is substantially flush with the first inner heat sink face, and the second inner support face is substantially flush with the second inner heat sink face.

Clause 6. The UV light-emitting assembly of any of clauses 1-5, wherein the plurality of UV light emitters is configured to emit 222 nm wavelength UV light.

Clause 7. An ultraviolet (UV) light-emitting assembly for disinfecting one or more components, the assembly comprising: a plurality of UV light emitters; a first UV light emitter support seating the plurality of UV light emitters; a second UV light emitter support seating the plurality of UV light emitters, wherein the first UV light emitter support is spaced from the second UV light emitter support; a heat sink comprising an actively-cooled plate; a first thermally conductive and electrically insulating pad comprising a first upper face that contacts a first bottom face of the first UV light emitter support and a first lower face that contacts the actively-cooled plate; and a second thermally conductive and electrically insulating pad comprising a second upper face that contacts a second bottom face of the second UV light emitter support and a second lower face that contacts the actively-cooled plate.

Clause 8. The UV light-emitting assembly of clause 7, wherein the plurality of UV light emitters is configured to emit 222 nm wavelength UV light.

Clause 9. An ultraviolet (UV) light-emitting assembly for varying UV light intensity emitted by a plurality of UV light emitters, the assembly comprising: a plurality of UV light emitters; a first UV light emitter support seating the plurality of UV light emitters; a second UV light emitter support seating the plurality of UV light emitters, wherein the first UV light emitter support is spaced by a gap from the second UV light emitter support; and a moving mechanism configured to vary the gap between the first UV light emitter support and the second UV light emitter support to change the UV light intensity of UV light emitted from the plurality of UV light emitters.

Clause 10. The UV light-emitting assembly of clause 9, wherein the moving mechanism is configured to translate the first UV light emitter support in a first direction and translate the second UV light emitter support in a second direction opposite to the first direction.

Clause 11. The UV light-emitting assembly of clause 9 or 10, wherein the moving mechanism is configured to translate only the first UV light emitter support or the second UV light emitter support.

Clause 12. The UV light-emitting assembly of any of clauses 9-11, further comprising a first heat sink affixed to the first UV light emitter support and a second heat sink affixed to the second UV light emitter support.

Clause 13. The UV light-emitting assembly of clause 12, wherein the first heat sink comprises a first plurality of fins extending from a first base portion, and the second heat sink comprises a second plurality of fins extending from a second base portion.

Clause 14. The UV light-emitting assembly of clause 13, wherein the first base portion is affixed to a first bottom face of the first UV light emitter support, and the second base portion is affixed to a second bottom face of the second UV light emitter support.

Clause 15. The UV light-emitting assembly of clause 13 or 14, wherein each fin of the first plurality of fins comprises a first distal end opposite to the first base portion, each fin of the second plurality of fins comprises a second distal end opposite to the second base portion, and the UV light assembly further comprises a thermally conductive and electrically insulating plate 370 contacting the first plurality of fins at their first distal ends and contacting the second plurality of fins at their second distal ends.

Clause 16. The UV light-emitting assembly of clause 15, wherein the moving mechanism is configured to translate the first heat sink relative to the thermally conductive and electrically insulating plate and to translate the second heat sink relative to the thermally conductive and electrically insulating plate.

Clause 17. The UV light-emitting assembly of any of clauses 12-16, wherein the first UV light emitter support comprises a first inner support face that faces a second inner support face of the second UV light emitter support, the first heat sink comprises a first inner heat sink face that faces a second inner heat sink face of the second heat sink, the first inner support face is substantially flush with the first inner heat sink face, and the second inner support face is substantially flush with the second inner heat sink face.

Clause 18. The UV light-emitting assembly of any of clauses 9-11, further comprising: a heat sink comprising an actively-cooled plate; a first thermally conductive and electrically insulating pad comprising a first lower face that contacts the actively-cooled plate and a first upper face that contacts a first bottom face of the first UV light emitter support; and a second thermally conductive and electrically insulating pad comprising a second lower face that contacts the actively-cooled plate and a second upper face that contacts a second bottom face of the second UV light emitter support.

Clause 19. The UV light-emitting assembly of any of clauses 9-18, wherein the plurality of UV light emitters is configured to emit 222 nm wavelength UV light.

Clause 20. A method for varying UV light intensity emitted by a plurality of UV light emitters, the method performed using a first UV light emitter support seating the plurality of UV light emitters and a second UV light emitter support seating the plurality of UV light emitters, wherein the first UV light emitter support is spaced from the second UV light emitter support, the method comprising: energizing the plurality of UV light emitters to emit a first UV light intensity when the first UV light emitter support is spaced from the second UV light emitter support by a first gap; moving the first UV light emitter support away from the second UV light emitter support until the first UV light emitter support is spaced from the second UV light emitter support by a second gap greater than the first gap; and energizing the plurality of UV light emitters to emit a second UV light intensity greater than the first UV light intensity when the first UV light emitter support is spaced from the second UV light emitter support by a second gap.

Clause 21. The method of clause 20, wherein moving the first UV light emitter support away from the second UV light emitter support comprises translating the first UV light emitter support in a first direction and translating the second UV light emitter support in a second direction opposite to the first direction.

Clause 22. The method of clause 21, wherein moving the first UV light emitter support away from the second UV light emitter support comprises translating only the first UV light emitter support.

The subject disclosure includes all novel and non-obvious combinations and subcombinations of the various features and techniques disclosed herein. The various features and techniques disclosed herein are not necessarily required of all examples of the subject disclosure. Furthermore, the various features and techniques disclosed herein may define patentable subject matter apart from the disclosed examples and may find utility in other implementations not expressly disclosed herein.

The invention claimed is:
1. An ultraviolet (UV) light-emitting assembly for varying UV light intensity emitted by a plurality of UV light emitters for disinfecting one or more components, the assembly comprising:
 a plurality of UV light emitters;
 a first UV light emitter support moveably seating the plurality of UV light emitters;
 a second UV light emitter support moveably seating the plurality of UV light emitters, wherein the first UV light emitter support is spaced by a gap from the second UV light emitter support; and
 one or more actuators configured to vary the gap between the first UV light emitter support and the second UV light emitter support to change a UV light intensity of UV light emitted from the plurality of UV light emitters by translating at least one of the first UV light emitter support and the second UV light emitter support to cause relative movement between the at least one of the first UV light emitter support and the second UV light emitter support and the plurality of UV light emitters.

2. The UV light-emitting assembly of claim 1, wherein the one or more actuators are configured to translate the first UV light emitter support in a first direction and translate the second UV light emitter support in a second direction opposite to the first direction.

3. The UV light-emitting assembly of claim 1, wherein the one or more actuators are a single actuator configured to translate only the first UV light emitter support or the second UV light emitter support.

4. The UV light-emitting assembly of claim 1, further comprising a first heat sink affixed to the first UV light emitter support and a second heat sink affixed to the second UV light emitter support.

5. The UV light-emitting assembly of claim 4, wherein the first heat sink comprises a first plurality of fins extending from a first base portion, and the second heat sink comprises a second plurality of fins extending from a second base portion.

6. The UV light-emitting assembly of claim 5, wherein the first base portion is affixed to a first bottom face of the first UV light emitter support, and the second base portion is affixed to a second bottom face of the second UV light emitter support.

7. The UV light-emitting assembly of claim 5, wherein each fin of the first plurality of fins comprises a first distal end opposite to the first base portion, each fin of the second plurality of fins comprises a second distal end opposite to the second base portion, and the UV light-emitting assembly further comprises a thermally conductive and electrically insulating plate contacting the first plurality of fins at their first distal ends and contacting the second plurality of fins at their second distal ends.

8. The UV light-emitting assembly of claim 7, wherein the one or more actuators are configured to translate the first heat sink relative to the thermally conductive and electrically insulating plate and to translate the second heat sink relative to the thermally conductive and electrically insulating plate.

9. The UV light-emitting assembly of claim 4, wherein the first UV light emitter support comprises a first inner support face that faces a second inner support face of the second UV light emitter support, the first heat sink comprises a first inner heat sink face that faces a second inner heat sink face of the second heat sink, the first inner support face is substantially flush with the first inner heat sink face, and the second inner support face is substantially flush with the second inner heat sink face.

10. The UV light-emitting assembly of claim 1, further comprising:
a heat sink comprising an actively-cooled plate;
a first thermally conductive and electrically insulating pad comprising a first lower face that contacts the actively-cooled plate and a first upper face that contacts a first bottom face of the first UV light emitter support; and
a second thermally conductive and electrically insulating pad comprising a second lower face that contacts the actively-cooled plate and a second upper face that contacts a second bottom face of the second UV light emitter support.

11. The UV light-emitting assembly of claim 1, wherein the plurality of UV light emitters is configured to emit 222 nm wavelength UV light.

12. A method for varying UV light intensity emitted by a plurality of UV light emitters, the method performed using a first UV light emitter support moveably seating the plurality of UV light emitters and a second UV light emitter support moveably seating the plurality of UV light emitters, wherein the first UV light emitter support is spaced from the second UV light emitter support, the method comprising:
energizing the plurality of UV light emitters using a first power to emit a first UV light intensity when the first UV light emitter support is spaced from the second UV light emitter support by a first gap;
moving the first UV light emitter support away from the second UV light emitter support by causing one or more actuators to translate at least one of the first UV light emitter support and the second UV light emitter support to cause relative movement between the at least one of the first UV light emitter support and the second UV light emitter support and the plurality of UV light emitters until the first UV light emitter support is spaced from the second UV light emitter support by a second gap greater than the first gap; and
energizing the plurality of UV light emitters using the first power to emit a second UV light intensity greater than the first UV light intensity when the first UV light emitter support is spaced from the second UV light emitter support by the second gap.

13. The method of claim 12, wherein moving the first UV light emitter support away from the second UV light emitter support comprises causing the one or more actuators to translate the first UV light emitter support in a first direction and causing the one or more actuators to translate the second UV light emitter support in a second direction opposite to the first direction.

14. The method of claim 13, wherein moving the first UV light emitter support away from the second UV light emitter support comprises causing one or more actuators to translate only the first UV light emitter support.

15. The method of claim 12, wherein a first heat sink is affixed to the first UV light emitter support and a second heat sink affixed to the second UV light emitter support.

16. The method of claim 15, wherein the first heat sink comprises a first plurality of fins extending from a first base portion, and the second heat sink comprises a second plurality of fins extending from a second base portion.

17. The method of claim 16, wherein the first base portion is affixed to a first bottom face of the first UV light emitter support, and the second base portion is affixed to a second bottom face of the second UV light emitter support.

18. The method of claim 16, wherein each fin of the first plurality of fins comprises a first distal end opposite to the first base portion, each fin of the second plurality of fins comprises a second distal end opposite to the second base portion, and a thermally conductive and electrically insulating plate contacts the first plurality of fins at their first distal ends and contacts the second plurality of fins at their second distal ends.

19. The method of claim 18, wherein the one or more actuators is configured to translate the first heat sink relative to the thermally conductive and electrically insulating plate and to translate the second heat sink relative to the thermally conductive and electrically insulating plate.

20. The method of claim 15, wherein the first UV light emitter support comprises a first inner support face that faces a second inner support face of the second UV light emitter support, the first heat sink comprises a first inner heat sink face that faces a second inner heat sink face of the second heat sink, the first inner support face is substantially flush with the first inner heat sink face, and the second inner support face is substantially flush with the second inner heat sink face.

21. The method of claim 12, wherein a first bottom face of the first UV light emitter support is contacted by a first upper face of a first thermally conductive and electrically insulating pad that comprises a first lower face that contacts an actively-cooled plate of a heat sink, and a second bottom face of the second UV light emitter support is contacted by a second upper face of a second thermally conductive and electrically insulating pad that comprises a second lower face that contacts the actively-cooled plate of the heat sink.

22. The method of claim 12, wherein the plurality of UV light emitters is configured to emit 222 nm wavelength UV light.

\* \* \* \* \*